United States Patent [19]

O'Donnell

[11] Patent Number: 5,669,903
[45] Date of Patent: Sep. 23, 1997

[54] OSTIOMEATAL COMPLEX SINUS CRYOSURGICAL PROCEDURE

[76] Inventor: Eugene P. O'Donnell, 8038 S. Painter Ave., Whittier, Calif. 90602

[21] Appl. No.: 505,474

[22] Filed: Jul. 21, 1995

[51] Int. Cl.⁶ .................................................. A61B 17/36
[52] U.S. Cl. ........................ 606/20; 128/898; 606/21; 606/23
[58] Field of Search ................... 606/20–26; 128/898

[56] References Cited

U.S. PATENT DOCUMENTS

| | | | |
|---|---|---|---|
| 5,224,943 | 7/1993 | Goddard | 606/20 |
| 5,334,181 | 8/1994 | Rubinsky et al. | 606/20 |
| 5,403,309 | 4/1995 | Coleman et al. | 606/20 |

OTHER PUBLICATIONS

Elwany et al., "Inferior turbinectomy: Comparison of four techniques", Journal of Laryngology and Otology, vol. 104, pp.206–209 Mar. 1990.

Hartley et al, "Cryotherapy in the treatment of nasal obstruction: indications in adults", Journal of Laryngology and Otology, vol. 109, pp. 729–732 Aug. 1995.

*Primary Examiner*—Jennifer Bahr
*Assistant Examiner*—Michael Peffley
*Attorney, Agent, or Firm*—Edgar W. Averill, Jr.

[57] ABSTRACT

A process for removing obstructions to sinus drainage of patient. A cryoprobe cooled to about −100° C. is inserted into one nostril of the patient and lodged inferiorly against the bone and lateral wall of the nose of the patient. The is maintained in this position for a period of about 90 seconds. Then the cryoprobe is moved within the first nostril to superior position and lodged against the sphenoid bone and cribriform plate of the ethmoid bone of the patient and maintained for about 90 seconds. The cryoprobe is then inserted into the other nostril and placed in the above two mentioned positions with the result that sinus drainage is markedly improved as is the sense of smell.

1 Claim, 3 Drawing Sheets

OSTIOMEATAL COMPLEX SINUS CRYOSURGICAL PROCEDURE

BACKGROUND OF THE INVENTION

The field of the invention is surgical procedures and the invention relates more particularly to cryosurgery.

Many persons are bothered with sinus headaches associated with sinus problems. This is caused by the blockage of sinus drainage and in the past has been treated by painful sinus surgery performed with a scalpel. Unfortunately, such procedures have had limited effect because of concomitant scarring.

SUMMARY OF THE INVENTION

It is thus an object of the present invention to provide a surgical procedure for improving the drainage of a patient's sinus.

The present invention is for a process for removing obstructions to sinus drainage. The process involves the steps of inserting a cryoprobe into one of the patient's nostrils and lodging the cryoprobe in an inferior position against the sphenoid bone and the lateral wall of the nose of the patient. Next, the cryoprobe is lodged superiorly against the sphenoid bone and the nasal surface of the ethmoid bone of the patient. The cryoprobe which is cooled to about $-100°$ C. is maintained in each of these positions for about 90 seconds. Next, the cryoprobe is inserted into the other nostril and placed in the same two positions and maintained in each of these positions for about 90 seconds.

DESCRIPTION OF THE PREFERRED EMBODIMENTS

Figure 1:
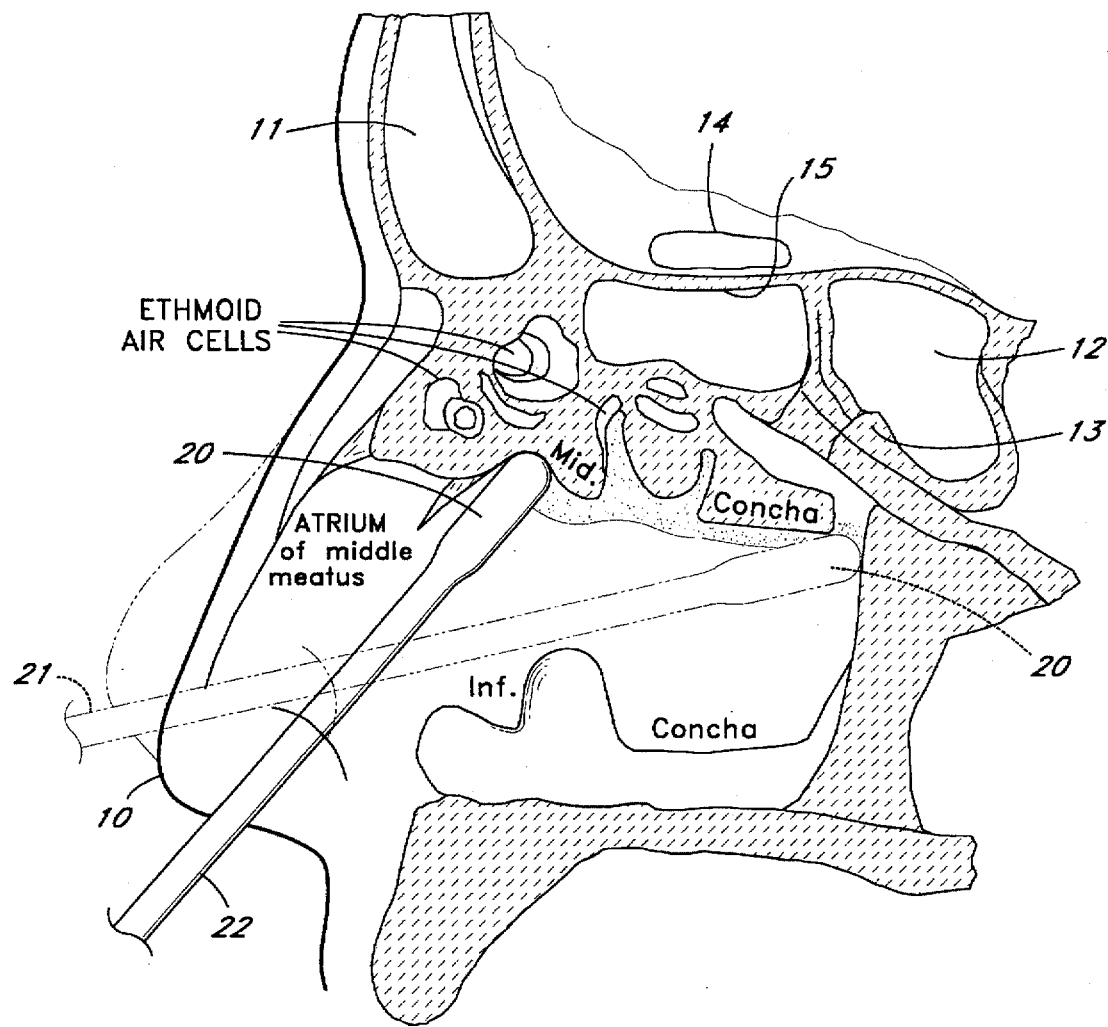
FIG. 1 is a diagrammatic view showing the paranasal air sinuses of a patient in cross-sectional view.

A patient's nose is shown in FIG. 1 in cross-sectional view. The exterior of the nose is indicated by reference character 10 and a frontal sinus by reference character 11. The sphenoidal sinus is indicated by reference character 12 and is separated from the interior of the nose by sphenoid bone 13. The olfactory bulb 14 is positioned above the cribriform plate 15.

Figure 2:
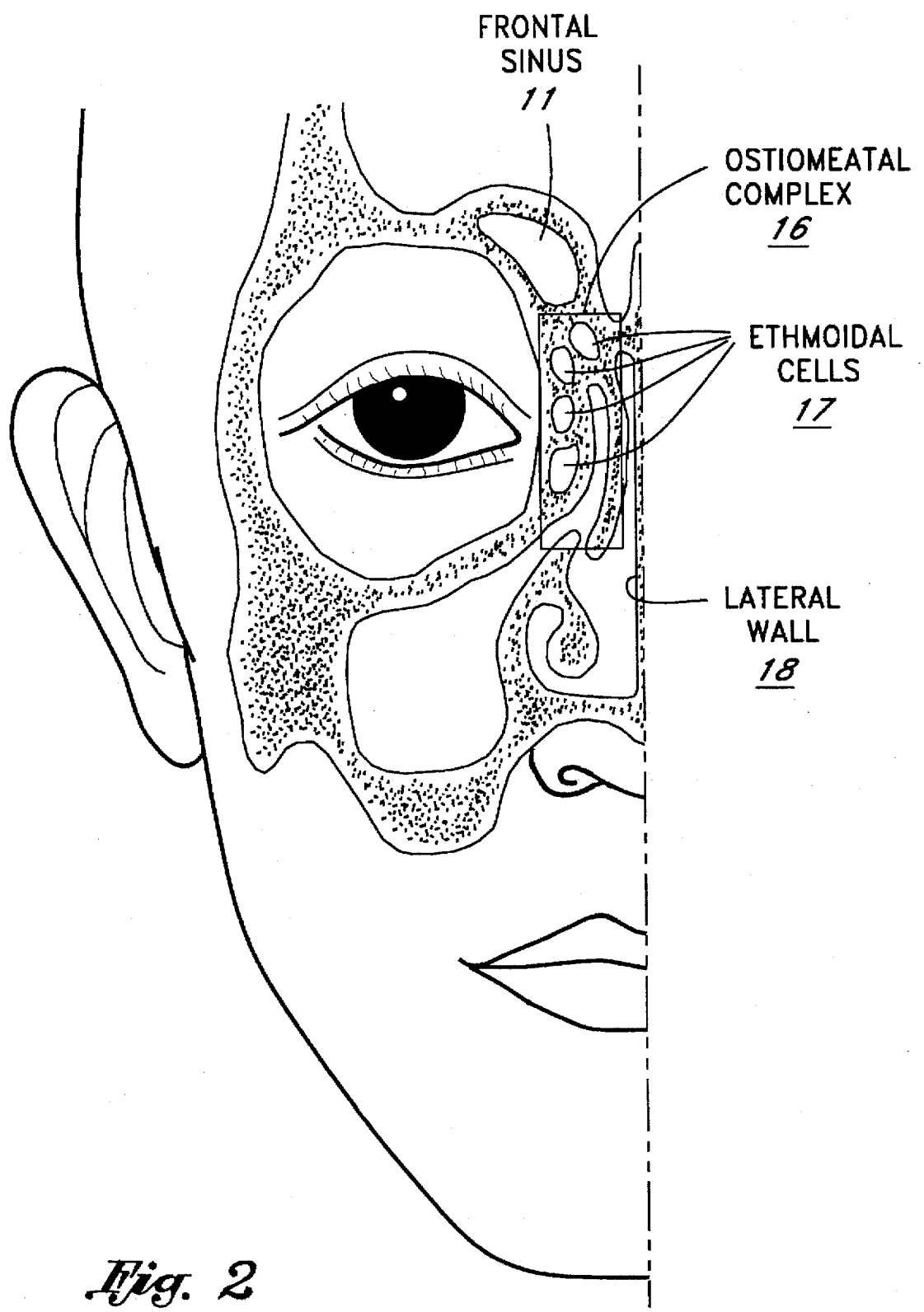
FIG. 2 is a front view of a patient's nose partly in cross-section.

In FIG. 2 the patient is shown from a front view. The frontal sinus is indicated again by reference character 11 and the ostiomeatal complex generally by reference character 16. The ethmoidal cells are indicated by reference character 17 and the lateral wall of the nose is indicated by reference character 18.

In order to perform the surgery the patient is placed on an operating table with the head elevated 30° proximally. 100 mg of Demerol, 50 mg of Vistaril and 10 mg of Valium are intravenously injected in a vein in the left antecubital fossa. Xylocaine jelly is placed on four swabs and two are placed on each side of the nose in the nasal cavity. One is placed superiorly and the other is placed inferiorly in the nasal cavity and left there for approximately 30 seconds. The sphenopalatine ganglion is blocked using 1.5 cc of Xylocaine with epinephrine as a local injection on both the right and left sides. A cryoprobe of the type shown in U.S. Pat. No. 3,696,813, but having a flat blade about 2.5 mm high, 25 mm long and 5 mm wide, is shown in FIG. 1 and indicated by reference character 20. The blade is firmly lodged superiorly in a position indicated by reference character 21 in FIG. 1 against the sphenoid bone and nasal surface of the ethmoid bone. With this placement the ostiomeatal complex is attacked to destroy the diseased and hypertrophic mucous membranes which are surrounding the ostia and narrowing the ostia. At the same time, polyps are being frozen completely and destroyed. The cryo ice ball (indicated by reference character 31 in FIG. 5) forms not only on the outside of the sinus ostium (on the nasal cavity side), but extends through the ostium to also destroy for a short distance, the mucous membrane inside the sinus cavity. It is especially important that this occurs which results in opening the ethmoid air cells to increase ventilation to the sinuses. It is believed that a portion of the bone proximal to the cryo tip is also destroyed and helps to increase the ventilation in the sinuses.

The olfactory bulb 14 is in this area and its nerve branches are affected by this freezing/destruction process so that healthy, unencumbered olfactory nerves are again exposed to more efficiently function again. This improves smell and improves the patient's sense of taste. The probe must be placed deep into the middle concha and firmly lodged against the lateral wall of the nose to extend the cryo destruction to a more posterior area of the ostiomeatal complex. Thus, it requires two distinct placements of the cryoprobe on each side of the nose to effect the destruction of all the diseased ostiomeatal complex tissues. The inferior placement is indicated by reference character 22 in FIG. 1. Of course, the placement in the second nostril is identical but a mirror image of that shown in FIG. 1.

The inferior turbinates are not destroyed and thus, problems of septal infection, necrosis and possible perforation of the septum is eliminated. The cryoprobe is maintained at a temperature of about $-100°$ C. while it is being used to destroy tissues in the nose. The time that the probe is placed with the freezing current on is 90 seconds. Each area is allowed to completely thaw and freeze again for 70 seconds.

The sphenoid bone, the midline nasal bone and the cribriform plate of the ethmoid bone, where the ethmoid air cells are located, are subjected to $-100°$ C. which causes the periosteum to necrose as well as the diseased mucosa overlying the bone. A thin layer just under the periosteum is also necrosed by this $-100°$ C. temperature. Therefore the bone is thinner and, most importantly at the ostium, the bony opening is enlarged all around the hole which increases the drainage aperture and increases ventilation of the entire ostiomeatal complex.

The repair of the bone surface that remains is recovered with new thin periosteum and mucous membrane with no fibroblastic activity to cause a scar to form and negate the opening up effects of this surgery. Scar formation after a cutting type surgery can result in worse drainage which does not happen with the cryosurgery method of the present invention.

Figure 3:
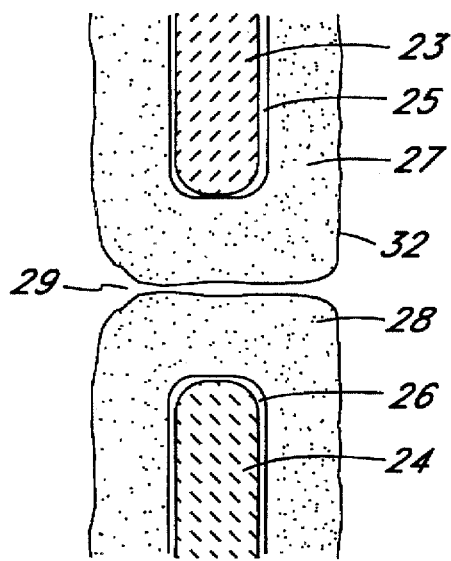
FIG. 3 is a cross-sectional diagrammatic view of a portion of the ostiomeatal complex showing thickened mucous membrane.
Figure 4:
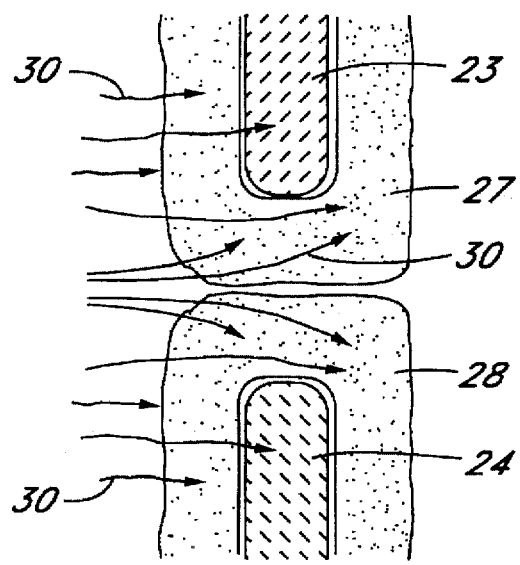
FIG. 4 is a diagrammatic cross-sectional view similar to FIG. 3 during a freezing process.
Figure 5:
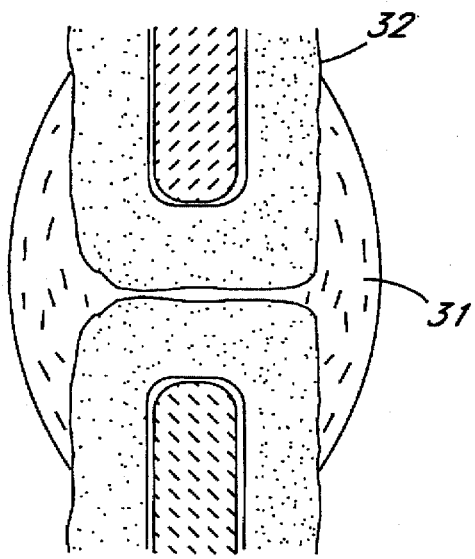
FIG. 5 is a diagrammatic cross-sectional view analogous to FIG. 3 after a freezing step.
Figure 6:
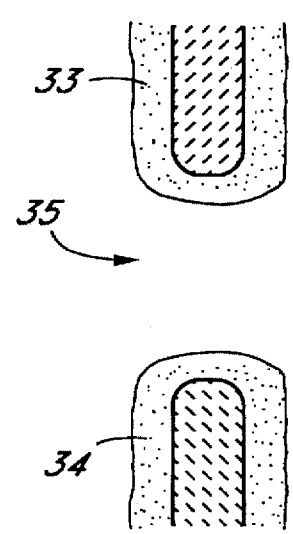
FIG. 6 is a diagrammatic cross-sectional view similar to FIG. 3 after recovery.

The process of the present invention is shown diagrammatically in FIGS. 3, 4, 5 and 6. A portion of the ostiomeatal complex is shown in FIG. 3 including bone portions 23 and 24 covered with periosteum 25 and 26. Periosteum 24 and 25 is covered with thickened mucous membrane 27 and 28 which essentially meet to cause near blockage or actual blockage of the sinus ostium 29. After contact with a cryoprobe at −100° C. such as cryoprobe 20 an ice ball 31 forms as indicated in FIG. 5. This ice ball extends to the sinus side 32 and also extends to a thin portion of the bone.

After ice ball 31 has melted the hypertrophic mucous membrane sloughs off in about 7–10 days. After a few days the mucous membrane regrows and the newly formed mucous membranes 33 and 34 are much thinner than mucous membranes 27 and 28 and a much enlarged sinus ostium 35 results. The process, thus, is able to treat areas which could not possibly be surgically reached without substantial destruction.

The present embodiments of this invention are thus to be considered in all respects as illustrative and not restrictive; the scope of the invention being indicated by the appended claims rather than by the foregoing description. All changes which come within the meaning and range of equivalency of the claims are intended to be embraced therein.

I claim:

1. A process for removing obstructions to sinus drainage of a patient having right and left nostrils comprising:

inserting a cryoprobe into one of said right and left nostrils and lodging said cryoprobe cooled to about −100° C. inferiorly against the sphenoid bone and the lateral wall of the nose of the patient;

maintaining the cryoprobe against the sphenoid bone and lateral wall of the nose of the patient for a period of about 90 seconds;

moving said cryoprobe in said one of said right and left nostrils to an superior position and lodging the cryoprobe cooled to about −100° C. superiorly against the sphenoid bone and the cribriform plate of the ethmoid bone of the patient;

maintaining the cryoprobe against the sphenoid bone and cribriform plate of the ethmoid bone for a period of about 90 seconds;

inserting a cryoprobe into the other of said right and left nostrils and lodging said cryoprobe cooled to about −100° C. inferiorly against the sphenoid bone and lateral wall of the nose of the patient;

maintaining the cryoprobe against the sphenoid bone and lateral wall of the nose of the patient for a period of about 90 seconds;

moving said cryoprobe in said other of said right and left nostrils to an superior position and lodging the cryoprobe cooled to about −100° C. superiorly against the sphenoid bone and the cribriform plate of the ethmoid bone of the nose of the patient;

maintaining the cryoprobe against the sphenoid bone for a period of about 90 seconds; and removing the cryoprobe.

* * * * *